(12) United States Patent
Chin et al.

(10) Patent No.: US 8,366,741 B2
(45) Date of Patent: Feb. 5, 2013

(54) OCCLUSION DEVICE WITH CENTERING ARM

(75) Inventors: Dara Chin, Saint Paul, MN (US); Michael P. Corcoran, Woodbury, MN (US); Joseph A. Marino, Apple Valley, MN (US)

(73) Assignee: Cardia, Inc., Eagan, MN (US)

( * ) Notice: Subject to any disclaimer, the term of this patent is extended or adjusted under 35 U.S.C. 154(b) by 1208 days.

(21) Appl. No.: 11/900,838

(22) Filed: Sep. 13, 2007

(65) Prior Publication Data

US 2009/0076541 A1   Mar. 19, 2009

(51) Int. Cl.
   *A61B 17/08* (2006.01)
(52) U.S. Cl. ......... 606/213; 606/139; 606/151; 606/232
(58) Field of Classification Search .......... 606/213–216, 606/139, 151, 157, 232
   See application file for complete search history.

(56) References Cited

U.S. PATENT DOCUMENTS

| | | |
|---|---|---|
| 3,874,388 A | 4/1975 | King et al. |
| 4,007,743 A | 2/1977 | Blake |
| 4,917,089 A | 4/1990 | Sideris |
| 5,108,420 A | 4/1992 | Marks |
| 5,171,259 A | 12/1992 | Inoue |
| 5,284,488 A | 2/1994 | Sideris |
| 5,334,137 A | 8/1994 | Freeman |
| 5,334,217 A | 8/1994 | Das |
| 5,350,399 A | 9/1994 | Erlebacher et al. |
| 5,382,260 A | 1/1995 | Dormandy, Jr. et al. |
| 5,397,331 A | 3/1995 | Himpens et al. |
| 5,425,744 A | 6/1995 | Fagain et al. |
| 5,433,727 A | 7/1995 | Sideris |
| 5,451,235 A | 9/1995 | Lock et al. |
| 5,601,595 A | 2/1997 | Smith |
| 5,634,936 A | 6/1997 | Linden et al. |
| 5,649,950 A | 7/1997 | Bourne et al. |
| 5,702,421 A | 12/1997 | Schneidt |
| 5,709,707 A | 1/1998 | Lock et al. |
| 5,725,552 A | 3/1998 | Kotula et al. |
| 5,733,294 A | 3/1998 | Forber et al. |
| 5,741,297 A | 4/1998 | Simon |
| 5,853,422 A | 12/1998 | Huebsch et al. |
| 5,904,703 A | 5/1999 | Gilson |

(Continued)

FOREIGN PATENT DOCUMENTS

DE   233 303 A1   2/1986
DE   4222291 A1   1/1994

(Continued)

OTHER PUBLICATIONS

Official Search Report and Written Opinion of the Patent Cooperation Treaty in counterpart foreign Application No. PCT/US08/10583, filed Sep. 11, 2008.

*Primary Examiner* — Corrine M McDermott
*Assistant Examiner* — Gregory Anderson
(74) *Attorney, Agent, or Firm* — Kinney & Lange, P.A.

(57) ABSTRACT

The present invention is an occlusion device having a centering arm network that self-centers across a defect and can be retrieved and redeployed in situ. A self centering system allows the center of the occlusion device to remain properly positioned within the defect, which increases the effectiveness of the occlusion device. The self centering system is comprised of a plurality of centering arms which define a flexible intermediate zone. In addition, the occlusion device of the present invention has a plurality of right arms connected to the plurality of centering arms which make it possible to retrieve and redeploy the occlusion device in situ.

20 Claims, 10 Drawing Sheets

U.S. PATENT DOCUMENTS

| | | | |
|---|---|---|---|
| 5,944,738 | A | 8/1999 | Amplatz et al. |
| 6,024,756 | A | 2/2000 | Huebsch et al. |
| 6,174,322 | B1 | 1/2001 | Schneidt |
| 6,206,907 | B1 | 3/2001 | Marino et al. |
| 6,261,309 | B1 | 7/2001 | Urbanski |
| 6,379,368 | B1 | 4/2002 | Corcoran et al. |
| 6,656,206 | B2 | 12/2003 | Corcoran et al. |
| 6,911,037 | B2 | 6/2005 | Gainor et al. |
| 6,960,220 | B2 | 11/2005 | Marino et al. |
| 6,960,224 | B2 | 11/2005 | Marino et al. |
| 2001/0044634 | A1 | 11/2001 | Don et al. |
| 2004/0143291 | A1 | 7/2004 | Corcoran et al. |
| 2005/0065546 | A1 | 3/2005 | Corcoran et al. |
| 2005/0065548 | A1 | 3/2005 | Marino et al. |

FOREIGN PATENT DOCUMENTS

| | | |
|---|---|---|
| EP | 0362113 A1 | 4/1990 |
| EP | 0541063 A3 | 5/1993 |
| EP | 0541063 B1 | 9/1998 |
| GB | 2269321 A | 2/1994 |

OCCLUSION DEVICE WITH CENTERING ARM

BACKGROUND

This invention relates to an occlusion device for the closure of physical apertures, such as vascular or septal apertures. More specifically, this invention relates to an occlusion device that self-centers across a defect and can be retrieved and redeployed in situ.

The heart is generally comprised of four chambers: the left and right atrium and the left and right ventricle. Separating the left and right sides of the heart are two walls, or septa. There are several defects which can affect the septa of both children and adults, including patent ductus arteriosus, patent foramen ovale, atrial septal defects (ASDs), and ventricular septal defects (VSDs). Although the causes and physical characteristics of these defects vary by type, these defects may generally comprise an aperture, flap, or hole in the septum which allows blood to shunt between chambers in the heart where there is no blood flow in a normal, healthy heart. This abnormal blood flow can cause a variety of health problems.

Normally, permanently repairing certain cardiac defects in adults and children requires open heart surgery, which is a risky, painful, and expensive procedure. Surgically closing an aperture in the heart requires the patient to undergo general anesthesia and requires opening of the chest cavity. The patient may spend several days in the hospital and may take several weeks to recover before being able to return to normal levels of activity.

To avoid the risks and discomfort associated with open heart surgery, modern occlusion devices have been developed that are small, implantable devices capable of being delivered to the heart through a catheter. Rather than surgery, a catheter inserted into a major blood vessel, and an occlusion device is moved through the catheter to the treatment site where it can then be deployed at the defect. This procedure is performed in a cardiac cathlab, and avoids the risks, pain, and long recovery associated with open heart surgery.

One type of occlusion device generally has a first side, which is positioned on one side of the defect, a second side, which is positioned on the opposite side of the defect, and a center section, which extends through the center of the defect. Since defect size varies from patient to patient, it is a challenge to center the center section within a particular defect, which is often essential to ensuring that the defect is optimally occluded. This is important because if the defect is not properly occluded, blood may continue to shunt through the defect lessening the effectiveness of the occlusion device.

Furthermore, many occlusion devices are designed so that the first and second sides are collapsible, allowing the occlusion device to fit inside a catheter. A catheter with a small diameter reduces trauma, improves maneuverability, and allows the occlusion device to be used in very young patients or in those who have a small vasculature. Therefore, it is desirable that the occlusion device be highly compact when in a collapsed position so that the smallest diameter catheter may be used for deployment.

However, loading the device into a small diameter catheter must be done by hand, which requires a high degree of manual dexterity, and can be time consuming. Also, in the event the device is not optimally deployed initially, it is desirable that it is easily retrievable, so that the procedure may be performed again. While some types of occlusion devices are retrievable via catheter, many require open heart surgery to be retrieved. Even in instances where the occlusion device can be retrieved using a catheter, a different catheter with a larger diameter may be required for retrieval because the device may not readily resume the compact shape it had before deployment. Furthermore, once retrieved, the device may be compromised from the stress of withdrawing it back into the catheter, even if a larger diameter catheter has been used. As such, it may not be possible to reuse the retrieved occlusion device.

In addition, occlusion devices retrieved via catheter are typically not properly loaded and positioned for redeployment. Thus, even if the occlusion device is retrievable, the device must be pulled back through the catheter and be completely removed from the catheter so that it can be properly reloaded. Reloading is time consuming, which adds additional time to the procedure, and also creates wear and tear on the device. Often, the retrieved device cannot be reused because it has been damaged by the retrieval process. If the device cannot be reused, a new device is required, which increases the cost of the procedure.

Thus, there is a need in the art for an occlusion device that is easily loaded into a catheter, and that can be retrieved, reloaded, and redeployed in situ. There is also a need in the art for an occlusion device which has a centering system to improve the ability of the device to be centered in the defect.

SUMMARY

The present invention is an occlusion device having a centering arm network that self-centers across a defect and can be retrieved and redeployed in situ. The self centering system allows the center of the occlusion device to remain properly positioned within the defect, which increases the effectiveness of the occlusion device. The self centering system is comprised of a plurality of centering arms which define a flexible intermediate zone. In addition, the occlusion device of the present invention has a plurality of right arms connected to the plurality of centering arms which make it possible to retrieve and redeploy the occlusion device in situ.

DETAILED DESCRIPTION

Figure 1A:
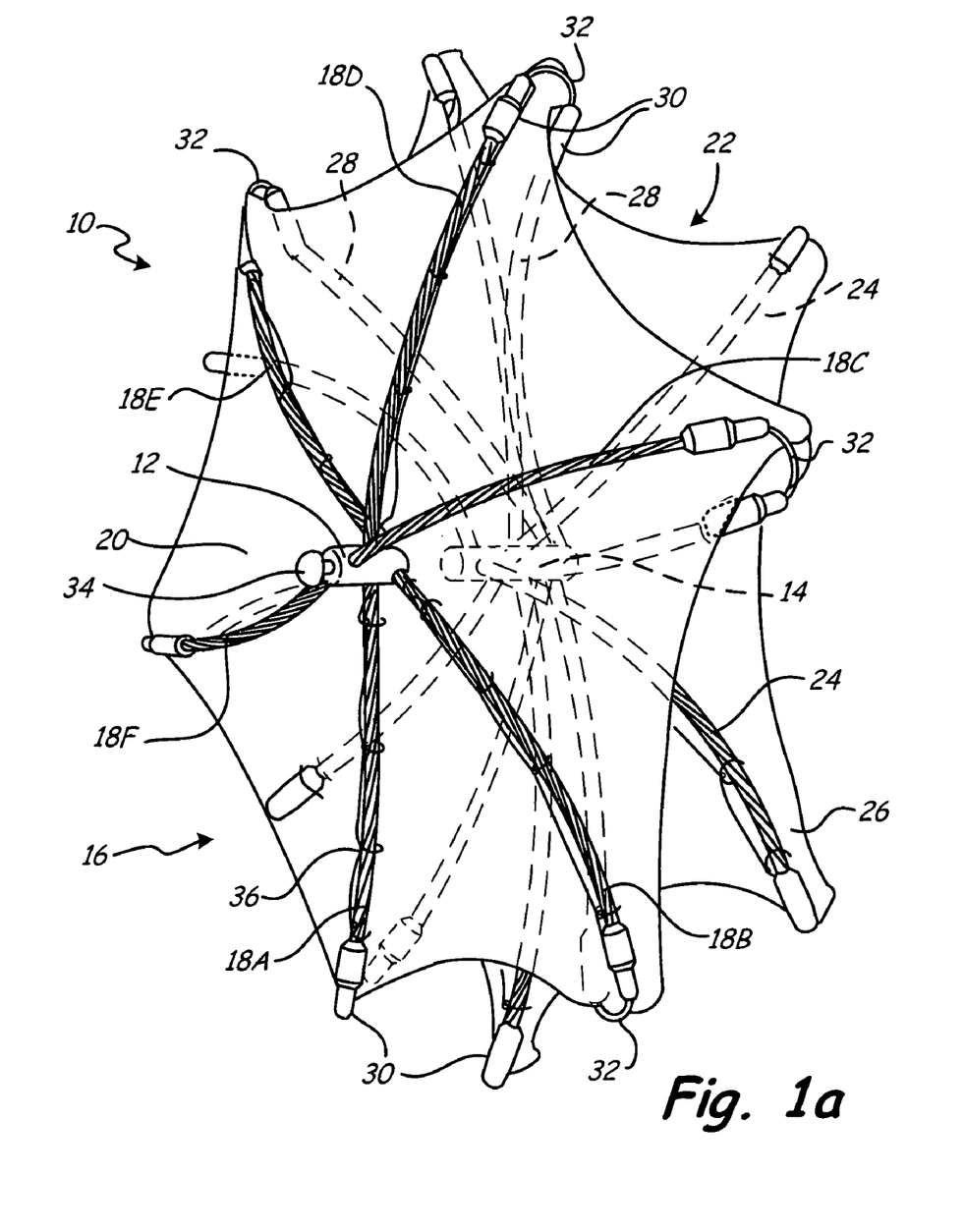
FIG. 1a is a perspective view of the right side of an occlusion device.

FIG. 1a is a perspective view of the right side of occlusion device 10. Occlusion device 10 comprises right center post 12, left center post 14, right occluding body 16, which includes right arms 18A-18F and right sheet 20, left occluding body 22, which includes left arms 24 and left sheet 26, and centering arms 28. Occlusion device also includes end caps 30, loops 32, grasping knob 34, and sutures 36. Portions of left occluding body 22, left arms 24, left sheet 26, and centering arms 28 are shown in dashed lines, as seen through right occluding body 16, and will be described in detail with respect to FIGS. 2 and 3.

Right occluding body 16 is connected to right center post 12. In the exemplary embodiment shown in FIG. 1a, right occluding body 16 includes six right arms 18A-18F. While occlusion device 10 is shown having six right arms 18A-18F, the invention is not so limited and right occluding body 16 may include more or less right arms 18A-18F. In order to keep the mass of occlusion device 10 minimal, however, occlusion device 10 preferably has a small number of right arms 18A-18F.

Right arms 18A-18F extend radially from right center post 12 and include end caps 30 at their tips. One method of connecting right arms 18A-18F to right center post 12 is to provide the right center post 12 with drill holes through which right arms 18A-18F pass. When connected to proximal center post 12 using holes drilled through the right center post 12, right arms 18A-18F may be formed of three wires. The three wires create the six right arms 18A-18F because right center post 12 divides each wire into two right arms 18A-18F when the wire passes through right center post 12. End caps 30, which are located at the distal ends of right arms 18A-18F serve to minimize damage to surrounding tissue once occlusion device 10 is deployed.

Right arms 18A-18F allow occlusion device 10 to be loaded or reloaded for deployment. Because delivery and retrieval occurs through the right chamber of the patient's heart, occlusion device 10 needs only to be graspable on the right side, which is attached to the delivery or retrieval device. For this reason, only one set of right arms 18A-18F is required. If desired, additional sets of right arms 18A-18F may be added, but the addition would increase the mass of occlusion device 10, which is often undesirable.

Another feature of occlusion device 10 is that it is fully retrievable. In situations where occlusion device 10 is not properly deployed and must be retrieved into the catheter, it is possible to withdraw occlusion device 10 back into the catheter by grasping knob 34 of right center post 12 and pulling. When tension is applied to right 1 center post 12 and, thus, to right arms 18A-18F, the right side of occluding device 10 (i.e. right occluding body 16) collapses and can be withdrawn into a catheter (as described in detail with reference to FIGS. 4a-4d). Subsequently, occlusion device 10 may be deployed or redeployed.

In the exemplary embodiment shown in FIG. 1a, right sheet 20 is attached to an inner side of right arms 18A-18F. However, the invention is not so limited and right sheet 20 may alternatively be attached to the proximal side of right arms 18A-18F. One method of attaching right sheet 20 to right arms 18A-18F is to suture right sheet 20 to right arms 18A-18F using sutures 36. However, right sheet 20 may be connected to right arms 18 using any suitable method, such as bonding, adhesive, heat treating, or laminating.

Grasping knob 34 is located at the tip of right center post 12. Grasping knob 34 is configured to allow occlusion device 10 to be grasped by a forceps or other delivery device as it is guided through a catheter. However, the method of attachment to a delivery device is not so limited and grasping knob 34 may be modified as needed to attach to any delivery device. For instance, grasping knob 34 may be formed with threads so that it may be screwed onto a corresponding delivery device. In addition, only one side of occlusion device 10 requires grasping knob 34 or other mechanism to attach to a delivery device.

Figure 1B:
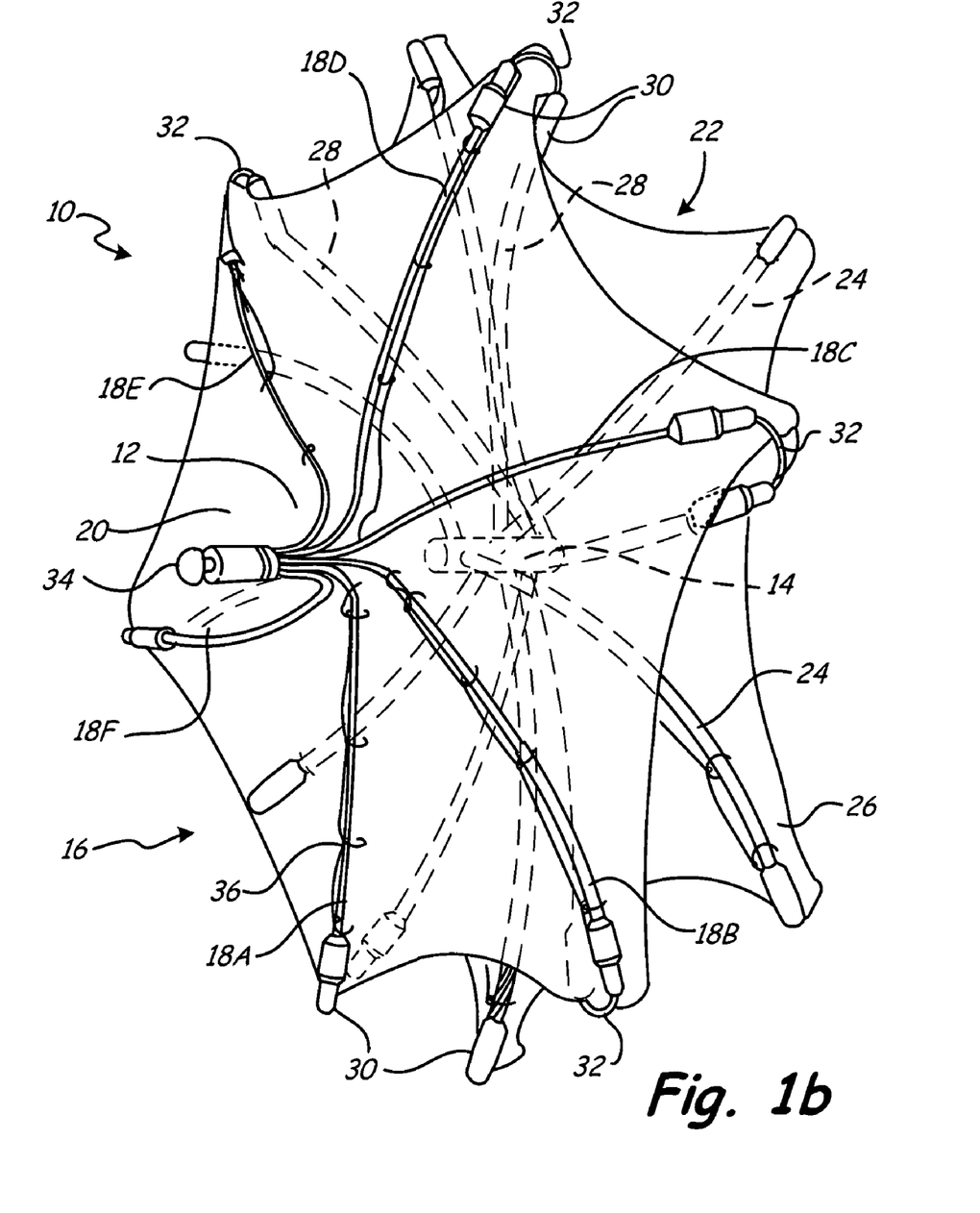
FIG. 1b is a perspective view of the right side of the occlusion device illustrating an alternate embodiment of the right arms.

FIG. 1b is a perspective view of the right side of the occlusion device illustrating an alternate embodiment of the right arms. Although, in FIG. 1a right arms 18A-18F are shown formed of stranded wires or cables, the invention is not so limited, and right arms 18A-18F may also be formed of single wires. Forming right arms 18A-18F of single wires may be desirable because the bend radius of right arms 18A-18F is increased. When right arms 18A-18F are formed of single wires, right arms 18A-18F may be attached to right center post 12 by inserting an end of each right arm 18A-18F into the distal end of right center post 12. This method of attachment requires that the distal end of right center post 12 is adapted to receive right arms 18A-18F. Thus, in the exemplary embodiment shown in FIG. 1b, the distal end of right center post 12 is hollow. Right arms 18A-18F are formed of six single stranded wires. An end of each right arm 18A-18F is inserted into the distal end of right center post 12 so that right arms 18A-18F emanate from the right center post 12. The distal end of right center post 12 is then crimped to retain right arms 18A-18F.

Figure 2:
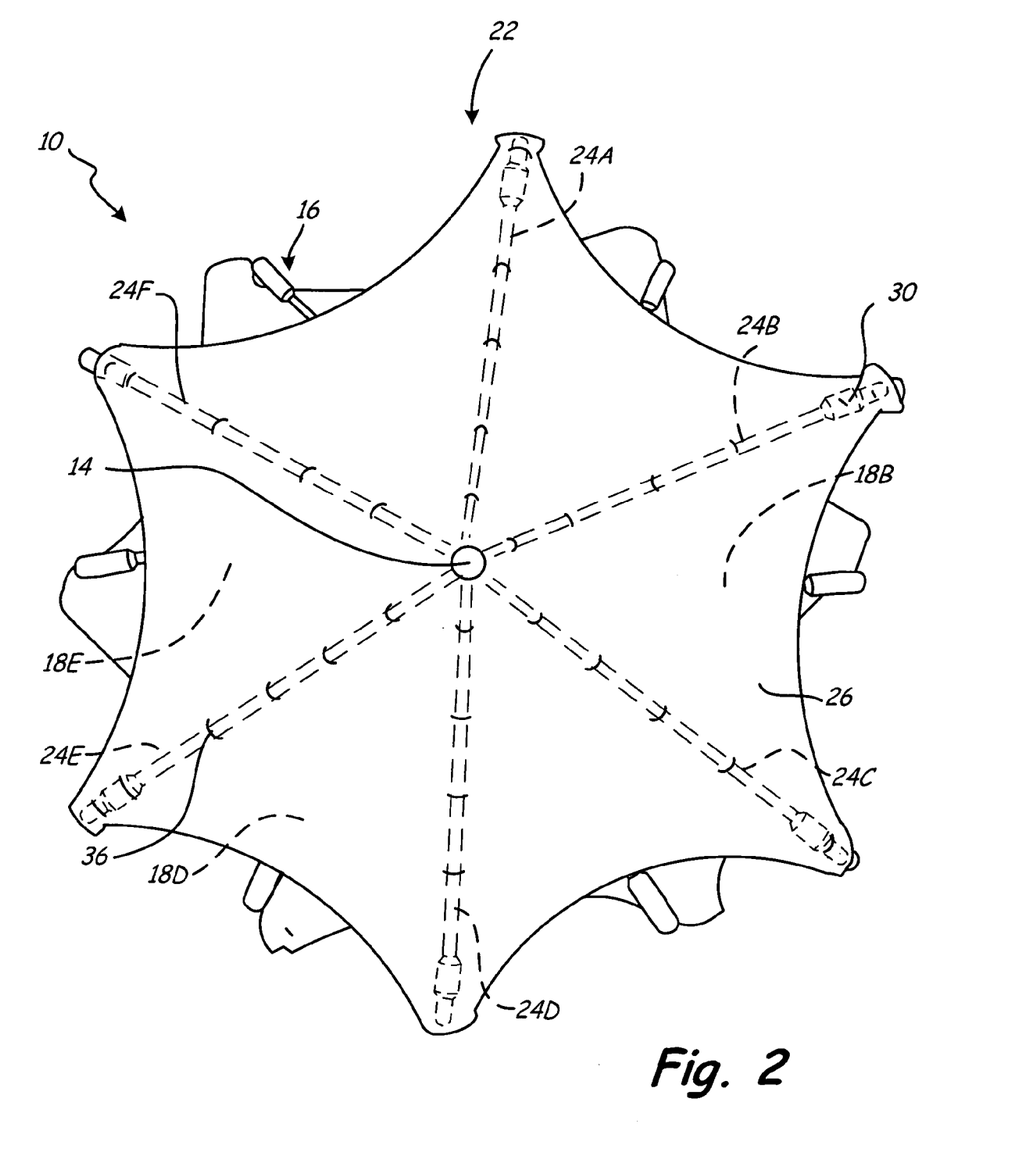
FIG. 2 is a perspective view of the left side of an occlusion device.

FIG. 2 is a perspective view of the left side of occlusion device 10. Shown are left center post 14, left occluding body 22, which includes left arms 24A-24F and left sheet 26, end caps 30 and sutures 26. Left arms 24A-24F and end caps 30 are shown in dashed lines, as seen though left sheet 26. Also partially visible in FIG. 2 is right occluding body 16.

Left occluding body 22 is connected to left center post 14. In the exemplary embodiment shown in FIG. 2, left occluding body 22 includes six left arms 24A-24F. While occlusion device 10 is shown having six left arms 24A-24F, the invention is not so limited and left occluding body 22 may include more or less left arms 24A-24F. However, once again, in order to minimize the mass, occlusion device 10 preferably has a small number of left arms 24A-24F.

Left arms 24A-24F extend radially from the proximal end of left center post 14 and include end caps 30 at their tips. As explained with respect to right arms 18A-18F in reference to FIG. 1, one method of connecting left arms 24A-24F to left center post 14 is to provide the left center post 14 with drill holes through which left arms 24A-24F pass. When connected to left center post 14 using holes drilled through the left center post 14, left arms 24A-24F may be formed of three wires. End caps 30 are located at the distal ends of left arms 24A-24F.

Unlike right arms 18A-18F, which are located on an outer side of right sheet 20, in the exemplary embodiment shown in FIG. 2, left arms 24A-24F are located on an inner side of left sheet 26. Sutures 36 are used to attach left sheet 26 to left arms 24A-24F. However, left sheet 26 may be connected to left arms 24A-24F using any suitable method.

Sheets 20, 26 may be formed of any suitable medical grade polymer, such as DACRON7. Preferably, sheets 20, 26 are formed of a high density polyvinyl alcohol (PVA) foam, such as that offered under the trademark IVALON7. To minimize the chance of occlusion device 10 causing a blood clot, sheets 20, 26 may be treated with a thrombosis-inhibiting material, such as heparin.

The size of sheets 20, 26 may vary to accommodate various sizes of defects. In some instances, it may be desirable to form sheets 20, 26 so that they are not both the same size. This is particularly useful in situations where occlusion device 10 is to be placed at a location in the heart which is close to other nearby cardiac structures. Making sheets 20, 26 different sizes may assist in providing optimal occlusion of a defect, without affecting other structures of the heart which may be nearby.

The other components of occlusion device 10 are likewise formed of suitable materials. More specifically, right and left center posts 12, 14 may be formed of platinum-iridium or titanium, and end caps 30 may be formed of titanium. Right arms 18A-18F and left arms 24A-24F may be made of Nitinol, platinum-iridium, or titanium. However, the invention is not limited to these materials and any suitable biocompatible materials will suffice.

Though not immediately evident in FIGS. 1 and 2, right arms 18A-18F and left arms 24A-24F may vary slightly in length. To allow occlusion device 10 to be retrievable and to ensure that occlusion device 10 fits into as small a diameter catheter as possible, it is important that right arms 18A-18F and left arms 24A-24F are not of a length that results in end caps 30 clustering at the same location when loaded inside the catheter. If end caps 30 are clustered in the same location when occlusion device 10 is inside the catheter, occlusion device 10 may become too bulky to allow it to be easily moved through the catheter. Thus, varying the length of right arms 18A-18F and left arms 24A-24F allows occlusion device 10 to fit more easily into a small diameter catheter when occlusion device 10 is folded (as shown in FIGS. 4a-4d) because end caps 30 do not cluster together.

Since occlusion device 10 is configured to be deployed through a catheter, right and left occluding bodies 16, 22 are easily collapsible about right and left center posts 12, 14, respectively, to allow occlusion device 10 to be inserted into and maneuvered through a catheter. Once occlusion device 10 is deployed across a cardiac defect, right arms 18A-18F and left arms 28A-28F and right and left sheets 20, 26 unfold to form a seal around each side of the defect. To ensure occlusion device 10 returns to a shape capable of exerting enough pressure to seal the defect, right arms 18A-18F and left arms 28A-28F are made of a suitable material capable of shape memory, such as nickel-titanium alloy, commonly called Nitinol. Nitinol is preferably used because it is commercially available, very elastic, non-corrosive and has a fatigue life greater than that of stainless steel. To further ensure that right arms 18A-18F and left arms 24A-24F do not suffer from fatigue failures, one embodiment of the present invention comprises making right arms 18A-18F and left arms 24A-24F of stranded wire or cables. However, the invention is not so limited and right arms 18A-18F and left arms 24A-24F may also be formed of single wires. (For example, in FIG. 1b, right arms are shown as formed from single wires.)

Right arms 18A-18F and left arms 24A-24B are preferably subjected to precise pre-shaping to give them a "shape memory." The pre-shaping can be done using any suitable method, such as machining, heat treating, or both. The shape memory helps to hold the strands together when right arms 18A-18F and left arms 24A-24F are formed of stranded wire or cable, and can be used to add pretension to right arms 18A-18F and left arms 24A-24F so that they "remember" their shape even after undergoing a strong deformation when occlusion device 10 is passed through a catheter. End caps 30 may further serve to prevent potential unraveling of right arms 18A-18F and left arms 24A-24F when formed of stranded wire or cable. Right arms 18A-18F and left arms 24A-24F may be formed to have identical or varying diameters.

Figure 3:
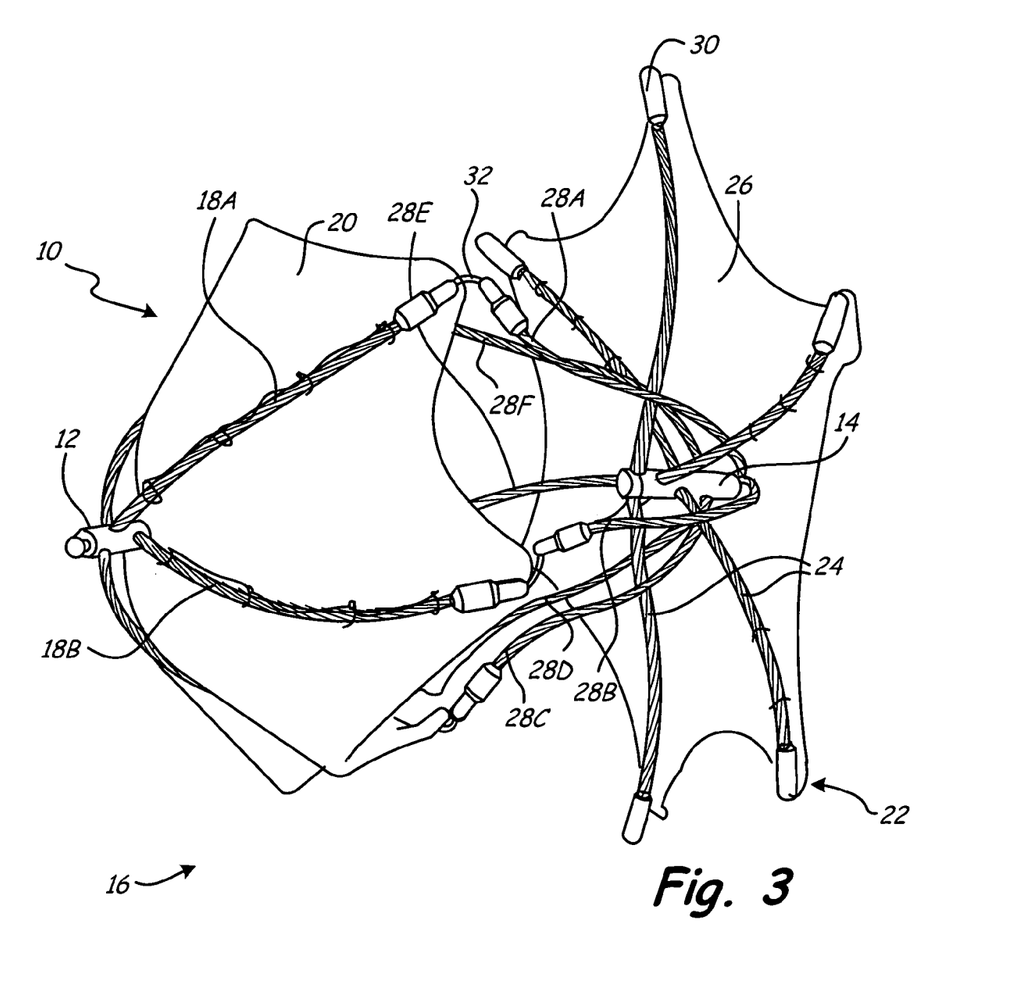
FIG. 3 is a perspective view of an occlusion device.

FIG. 3 is a perspective view of occlusion device 10 illustrating the position of centering arms 28A-28F, as right and left occluding bodies 16, 22 are tensioned apart. As explained with reference to FIG. 1, occlusion device 10 comprises right center post 12, left center post 14, right occluding body 16, which includes right arms 18A-18F and right sheet 20, left occluding body 22, which includes left arms 24A-24F and left sheet 26, and centering arms 28A-28F. End caps 30, loops 32, grasping knob 34, and sutures 36 can also be seen from this perspective.

Centering arms 28A-38F extend radially from left center post 14 and also include end caps 30 at their tips. In the exemplary embodiment shown in FIG. 3, occlusion device 10 is shown having six centering arms 28A-28F, which emanate from the distal end of left center post 14. However, the present invention is not so limited and occlusion device 10 may include more or less centering arms 28A-28F. Centering arms 28A-28F may be connected to distal center post 14 using any suitable method, such as providing left center post 14 with drill holes through which centering arms 28A-28F pass. (This method of attachment is described in detail with reference to right arms 18A-18F with respect to FIG. 1a.)

Centering arms 28A-28F are connected to right arms 18A-18F at their tips. In the exemplary embodiment shown in FIG. 3, centering arms 28A-28F and right arms 18A-18F are attached to each other with loops 32, which extend from end cap 30 of each centering arm 28A-28F to end cap 30 of a corresponding right arm 18A-18F. For instance, end cap 30 of centering arm 28A is connected to end cap 30 of right arm 18A, centering arm 28B is connected to end cap 30 of right arm 18B, and so on. Loops 32 are described in more detail with reference to FIG. 7a. In addition, loops 32 are just one possible method of connecting centering arms 28A-28F and right arms 18A-18F to each other. Another method of connecting centering arms 28A-28F and right arms 18A-18F is discussed with reference to FIG. 7b.

Like right arms 18A-18F and left arms 24A-24F, centering arms 28A-28F are preferably made of a flexible material, such as Nitinol, in the form of stranded wire or cables. In addition, centering arms 28A-28F are preferably subjected to precise pre-shaping to give them "shape memory", so that they "remember" their shape even after undergoing a strong deformation when occlusion device 10 is passed through a catheter. One suitable shape for centering arms 28A-28F is a bell shape. This shape allows occlusion device 10 to maintain a low profile once occlusion device 10 is deployed, and also allows centering arms 28A-28F to center occlusion device 10 within a defect.

Once occlusion device 10 is deployed, centering arms 28A-28D extend through the defect and define a flexible intermediate zone. Because centering arms 28A-28F are flexible, the diameter of the intermediate zone adjusts to the size of the defect but does not exert enough force to widen the diameter of the defect. In addition, the length of centering arms 28A-28F may be increased or decreased to better correspond to the size of the defect to be occluded. The curved upper portions of centering arms 28A-28F toward the distal end of occlusion device 10 have slight tension. The tension allows occlusion device 10 to self center because, if there is room in the defect for the upper portions of centering arms 28A-28F to widen, centering arms 28A-28F expand to accommodate the defect. Because the widening is symmetrical, occlusion device is capable of centering itself within the defect. In addition, if the defect is the defect is large, centering arms 28A-28D may expand to the same diameter of the defect and center occlusion device 10. If occlusion device 10 is properly centered, the likelihood that the defect will be sealed is increased and the likelihood of blood shunting is reduced.

Defects which can affect a heart's septum include patent foramen ovale, atrial septal defects (ASDs), and ventricular septal defects (VSDs) among others. Centering arms 28A-

28F may be pre-shaped according to what type of defect occlusion device 10 will be used to occlude. For example, a wide bell-like shape is usually ideal for occluding atrial septal defects (ASDs) and ventricular septal defects (VSDs), which are characterized by an actual hole and extend entirely through the septal wall. In contrast, a patent foramen ovale, which manifests itself as a flap of tissue between the right atrium and left atrium, is usually optimally occluded when centering arms 28A-28F have a narrower configuration.

FIGS. 4a-4d are diagrammatic views which demonstrate the automatic loading system of occlusion device 10. Though FIGS. 4a through 4d illustrate how to load occlusion device 10, the same procedure applies if occlusion device 10 must be retrieved, reloaded, and/or redeployed in situ.

Figure 4A:
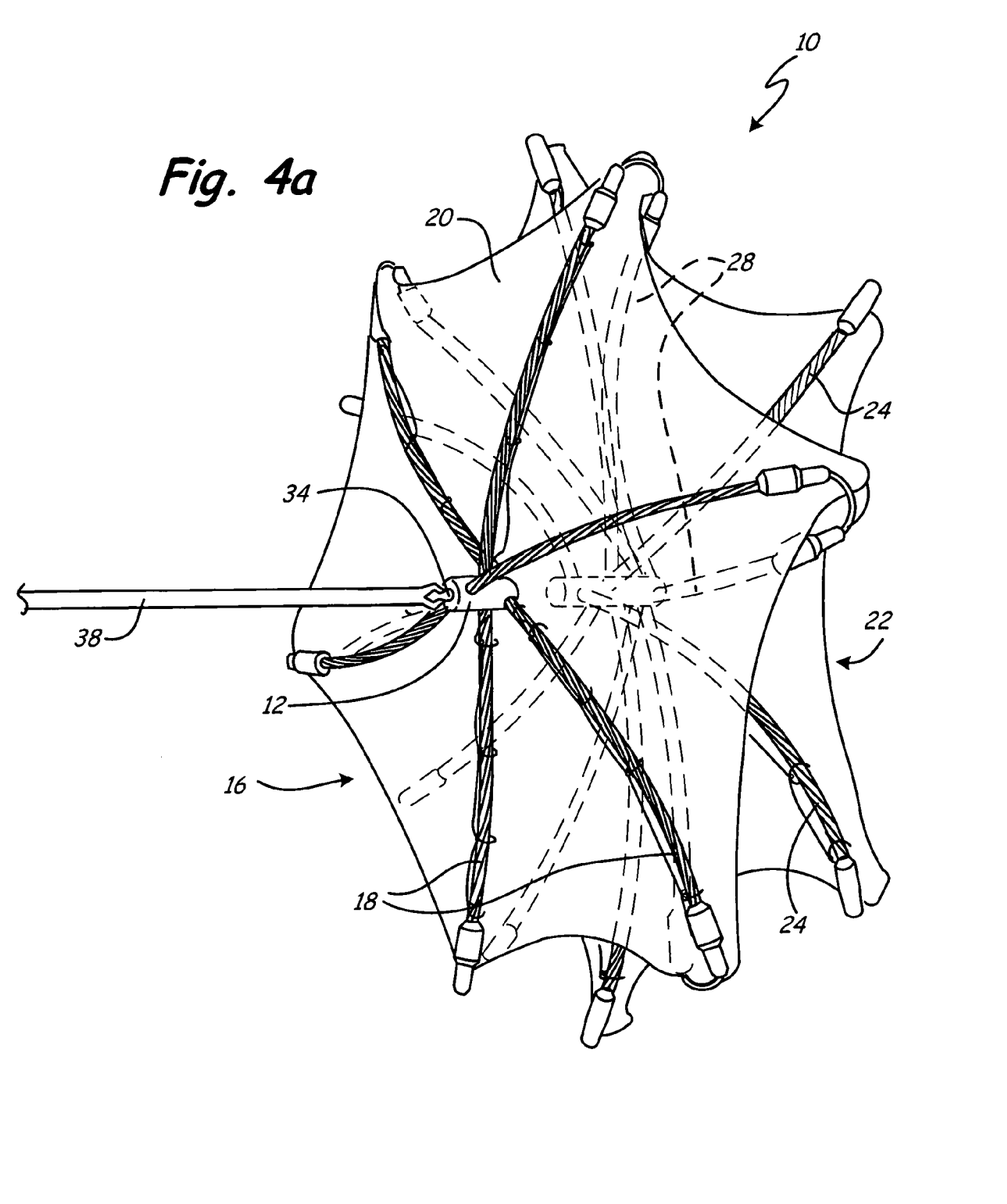
FIGS. 4a-4d are a diagrammatic series demonstrating how the occlusion device may be loaded or reloaded into a catheter.

FIG. 4a shows occlusion device 10, which comprises right occluding body 16 and left occluding body 22 connected by centering arms 28. Right occluding body 16 is so named because it is configured for placement in the right side of a patient's heart once occlusion device 10 is deployed. Left occluding body 22 is so named because it is configured for placement in the left side of a patient's heart once occlusion device 10 is deployed. Portions of occluding body 22 and centering arms 28 are shown in dashed lines as seen through right occluding body 16. In addition, a delivery device, forceps 38, is shown as attached to grasping knob 34.

FIG. 4a shows occlusion device 10 before occlusion device 10 is loaded into a catheter. Both left and right occluding bodies 16, 22 of occlusion device 10 are shaped to bias the edges of sheets 20, 26 inward. As a result, left and right occluding bodies 16, 22 each assume an umbrella-like shape. Shaping left and right occluding bodies 16, 22 with an inward bias helps ensure sheets 20, 26 fit snugly against the septum around the defect when occlusion device 10 is placed in the heart. The pressure exerted by left and right occluding bodies 16, 22 creates a seal around the defect. Forceps 38 includes a grasping mechanism for engaging and holding grasping knob 34, so that force can be applied to occlusion device 10 via forceps 38.

Figure 4B:
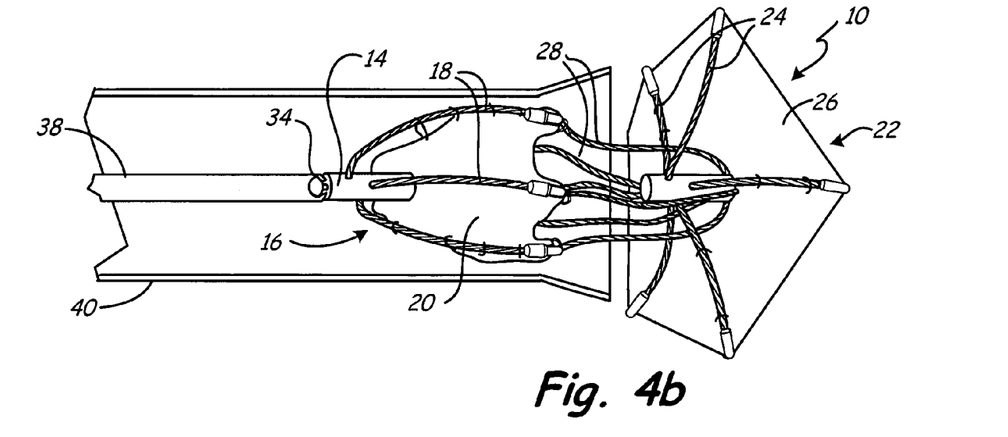
Figure 4C:
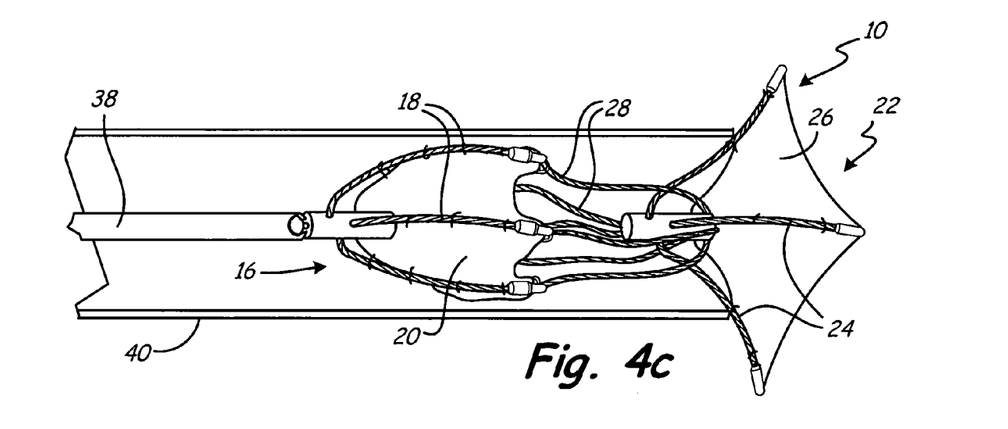
Figure 4D:
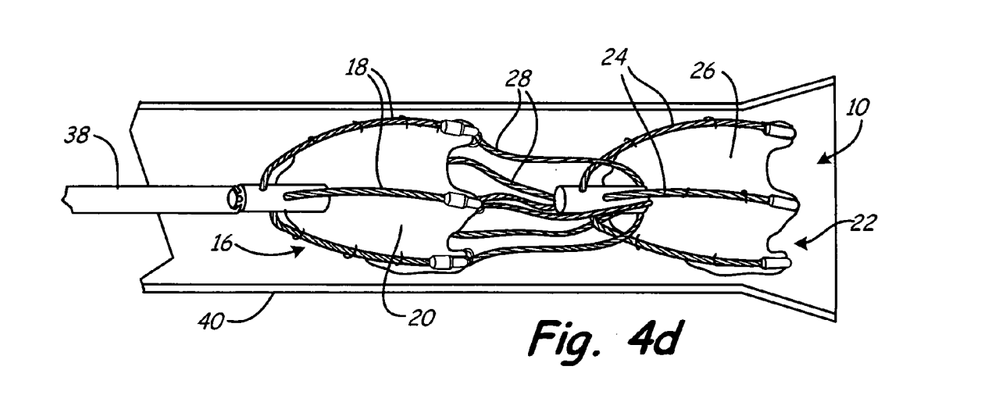

FIGS. 4b-4d illustrate the steps of loading occlusion device 10 into catheter 40. FIG. 4b illustrates the first step of loading occlusion device 10 into a catheter. After occlusion device 10 is grasped at knob 34 by forceps 38, as described with reference to FIG. 1, forceps 38 (or other suitable delivery device) is pulled into catheter 40. As shown in FIG. 4b, when a pulling force is applied to forceps 38, right center post 12, which is attached to grasping knob 34, moves away from left center post 14 toward the direction of the force. The movement of right center post 12 engages right arms 18 because right arms 18 are attached to proximal center post 12. Thus, right arms 18 lose curvature and begin to collapse inward, which also causes right sheet 20 to begin to fold. As forceps 38 is pulled farther into catheter 40, right arms 18 contact the rim of the fluted opening of catheter 40 and are forced to collapse even further. Right arms 18 and right sheet 20 continue to fold until right occluding body 16 has collapsed enough to be pulled entirely into catheter 40. Left occluding body 22 is still outside catheter 40 and is fully expanded.

In FIG. 4c, the pulling force continues to be transmitted from forceps 38 through right center post 12 and right arms 18 to centering arms 28. As right occluding body 16 is pulled deeper into catheter 40, centering arms 28 transmit the force to distal center post 14. When left center post 14 enters catheter 40, left arms 24, which are attached to the proximal end of left center post 14, contact the rim of catheter 40 and are forced to begin to collapse backward. As a result, left arms 24 no longer bias left sheet 26 forward and left sheet 26 also begins to invert and fold.

FIG. 4d shows occlusion device 10 completely loaded into catheter 40. As a result of the pressure applied by catheter 40, left arms 24 have continued to collapse backwards and finally straighten, which allows left occluding body 22 to also be pulled into catheter. Right and left occluding bodies 16, 22 are now both collapsed so that their end caps 30 are facing the opening of catheter 40. Right and left occluding bodies 16, 22 are maintained in this collapsed orientation by the constraints of catheter 40. At this point, occlusion device 10 is ready for deployment.

The design of the present invention allows occlusion device 10 to be loaded or reloaded easily, which has many advantages. The physician does not need to manually collapse occlusion device 10 to ready it for deployment, which makes initial loading easier. If occlusion device 10 has been deployed and must be retrieved and redeployed, the physician can retrieve, reload, and redeploy the device without first having to maneuver occlusion device 10 out of the body to be reloaded. Most devices do not automatically reload in the proper configuration when retrieved and thus, must be maneuvered back out of the patient's body to be reloaded for redeployment. When occlusion device 10 is pulled back through the catheter, out of the body, reloaded and redeployed, the integrity of occlusion device 10 may be compromised. Thus, it is preferable to be able to reload and redeploy occlusion device 10 without having to maneuver it through the patient's body again. In addition, the ability to reload and immediately redeploy occlusion device 10 reduces procedure time. Consequently, the present invention can save time, cost, and additional risk to the patient.

Figure 5:
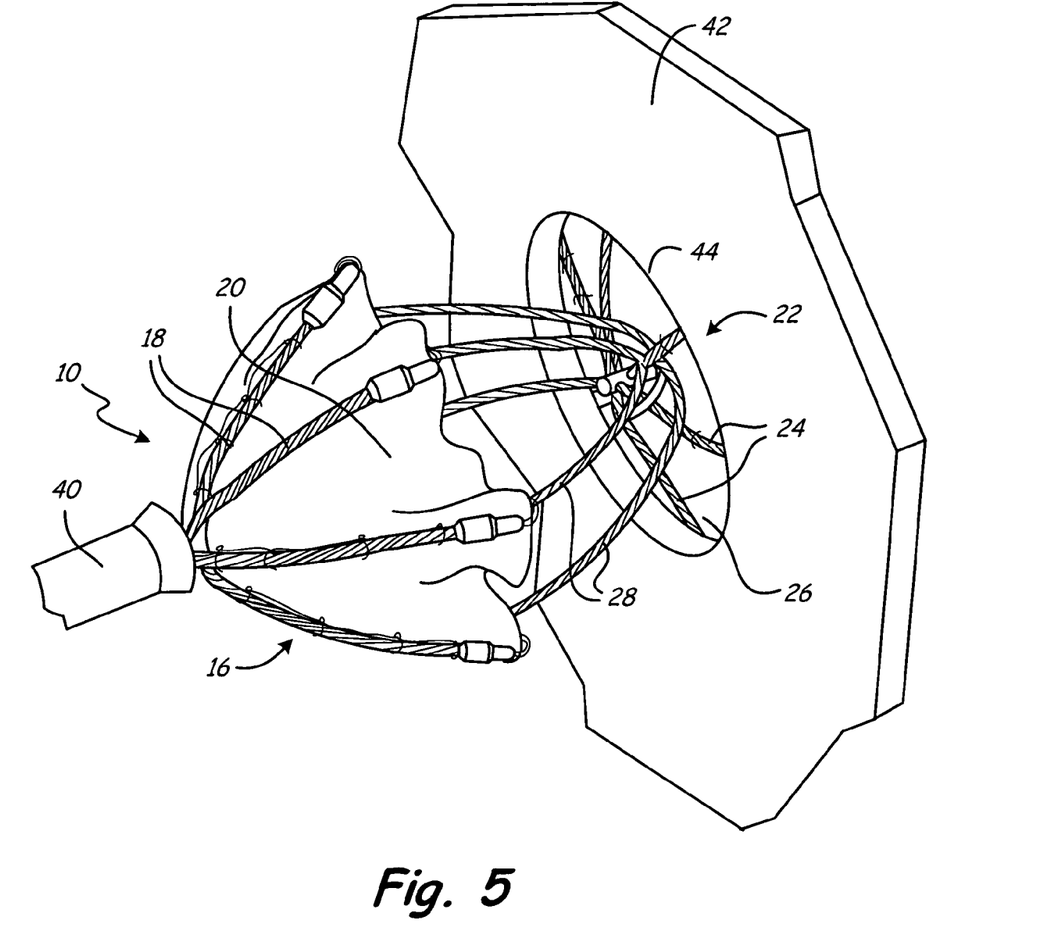
FIG. 5 illustrates the occlusion device as deployed across a septal defect.

FIG. 5 illustrates occlusion device 10 as deployed in septal wall 42 across defect 44. Left occluding body 22 is positioned on the distal side of septal wall 42. This was accomplished by inserting catheter 40 into defect 44. A physician may then advance occlusion device 10 through catheter 40 by using an appropriate delivery device, such as forceps 38, to apply a pushing force on occlusion device 10. When occlusion device 10 reaches the end of catheter 40, left occluding body 22 emerges. As left occluding body 22 exits the constraints of catheter 40, left arms 24 return to their pretensioned shape and left sheet 26 unfolds. Once left occluding body 22 is in position against septal wall 42, catheter 40 is withdrawn from defect 44 and right occluding body 16 is pushed forward. As right occluding body 16 exits catheter 40, right arms 18 return to their pretensioned shape, right sheet 20 unfolds, and right occluding body 16 is positioned on the proximal side of septal wall 42. Centering arms 28 extend through defect 44 and serve to center occlusion device 10 as discussed with reference to FIG. 3. As a result, right and left occluding bodies 16, 22 should effectively seal around each side of defect 44 and the unwanted blood flow will be restricted.

If occlusion device 10 should be positioned improperly across defect 44, the delivery device (i.e. forceps 38) can be used to grasp knob 34 located on right center post 12 and pull occlusion device 10 back into catheter 40. In doing so, both right and left occluding bodies 16, 22 will collapse as described with reference to FIGS. 4a-4d. Thus, occlusion device 10 will be ready for immediate redeployment. Once occlusion device 10 is properly positioned, the delivery device and catheter 40 are removed from the patient's body.

Figure 6:
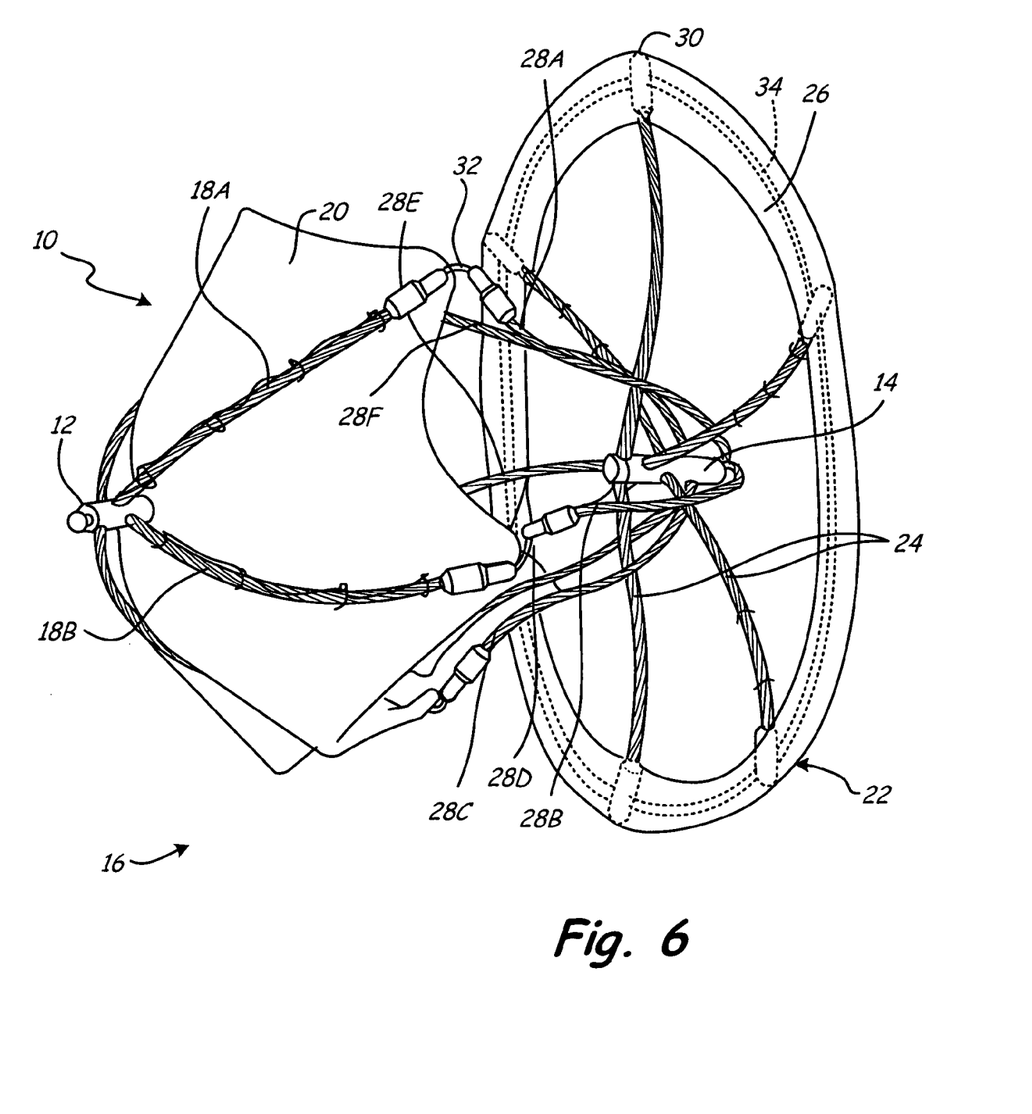
FIG. 6 is a perspective view of an occlusion device having a hoop on its left side.

FIG. 6 is a perspective view of occlusion device 10 having hoop 34 on its left side. Right occluding body 16 and center arms 28A-28F of occlusion device 10 are configured as described with reference to FIG. 1a. However, in the exemplary embodiment shown in FIG. 6, left occluding body 22 is configured to include hoop 34.

Hoop 34 extends around an outer perimeter of left occluding body 22 and is connected to left arms 24 using end caps 30, which are located at outer tips of left arms 24. One suitable method of attaching hoop 34 to end caps 30 is to pass hoop 34 through a hole drilled crosswise through each end cap 30. Hoop 34 is then closed so it forms a circle. Closure may be accomplished by securing the ends of hoop 34 in an end cap 30 at the location where the ends of hoop 34 meet. The ends of hoops 34 may secured using any suitable method, such as crimping, welding or adhesive. When hoop 34 is threaded through end caps 30 and closed, left arms 24 are essentially connected and move together as a unit.

Hoop 34 may be made of any suitable biocompatible material. However, hoop 34 is preferably made of a material capable of shape memory, such as Nitinol. In addition to ensuring that hoop 34 will resume the proper shape after leaving the catheter, shape memory also ensures that hoop 34 will lay flat against the tissue surrounding the defect once it is deployed.

One suitable method of attaching sheet 26 to hoop 34 is to form sheet 26 so that it has a larger diameter than hoop 34. The larger diameter of sheet 26 extends beyond hoop 34 after it is attached to left arms 24. Sheet 26 is then folded over hoop 34 to form a reinforced edge of double material around the perimeter of left occluding body 22. Once sheet 26 is folded over hoop 34, it can be secured in place by any suitable method, such as sutures, heat treatment or adhesive.

Including hoop 34 on the left side of occlusion device 10 makes it easier to properly position occlusion device during deployment. (Occlusion device 10 is deployed as described with reference to FIG. 5 regardless of whether left occluding body 22 includes hoop 34.) When occlusion device 10 is being deployed, left occluding body 22 exits the catheter first and is positioned against the septal wall on the distal side of the defect. The catheter is then withdrawn from the defect so right occluding body 16 can be deployed on the proximal side of the defect. Due to the topology of the heart, left occluding body 22 is seldom oriented in a position that is perpendicular to the defect during positioning. As a result, the outer tips of left arms 24 often make contact with the septal wall at different times. When this occurs, it is possible for one or more of left arms 24 to slip through the defect, which results in occlusion device 10 being improperly positioned. In addition, this can also occur when tension is applied to left occluding body 22 in order to withdraw the catheter back through the defect. Hoop 34 distributes pressure evenly among left arms 24, which makes it unlikely that a single arm 24 will poke through the defect. This pressure distribution also allows left occluding body 22 to create a more uniform seal around the distal side of the defect.

Figure 7A:
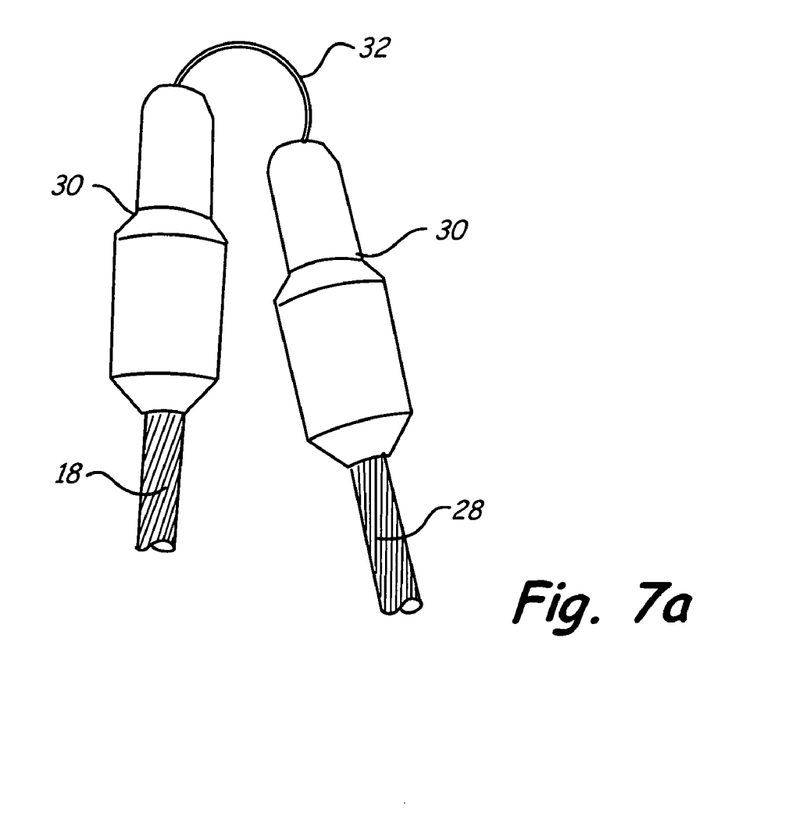
FIGS. 7a-7b demonstrate first and second exemplary embodiments for attaching a right arm to a centering arm.
Figure 7B:
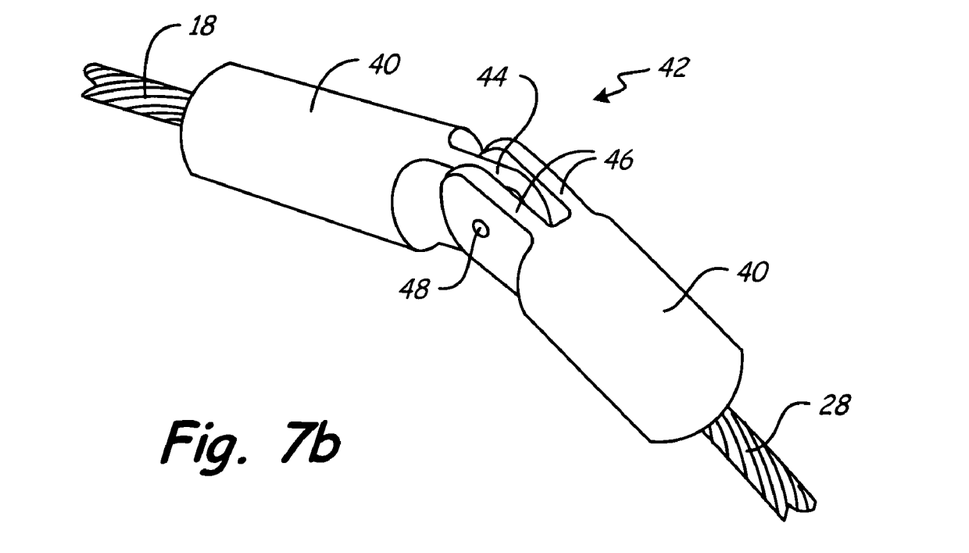

FIGS. 7a-7b demonstrate methods of attaching a right arm to a centering arm. FIG. 7a shows right arm 18 and centering arm 28 as connected with loop 32. In this exemplary embodiment, loop 32 extends from end cap 30 of right arm 18 to end cap 30 of corresponding centering arm 28. Loop 32 may be formed of a wire comprising any suitable material having the required strength and flexibility. One such suitable material is stainless steel. In addition, loop 32 may be formed of a solid wire or a stranded wire. When formed of a stranded wire, a 1×7 (one-by-seven) configuration may be used. A 1×7 stranded wire is formed by wrapping six wires around in individual component wire. Loop 32 may be attached to end caps 30 using any suitable attachment method. For instance, an end of wire loop 32 can be mechanically crimped to each of end caps 30.

FIG. 7b shows right arm 18 and centering arm 28, which are each capped with end caps 40, as connected with pivotal joint 42. In this exemplary embodiment, single prong 44 extends from the tip of end cap 40 attached to right arm 18 and double prongs 46 extend from the tip of end cap 40 to form a clevis attached to centering arm 28. (However, the present invention is not so limited, and double prongs 46 may extend from the tip of end cap 40 attached to right arm 18 and single prong 44 may extend from the tip of end cap 40 attached to centering arm 128.) Single prong 44 fits in between double prongs 46 and may be held in place by pin 48. Pivotal joint 42 provides enough range of motion and flexibility to allow the occlusion device to collapse for deployment and center itself within a defect.

Figure 8:
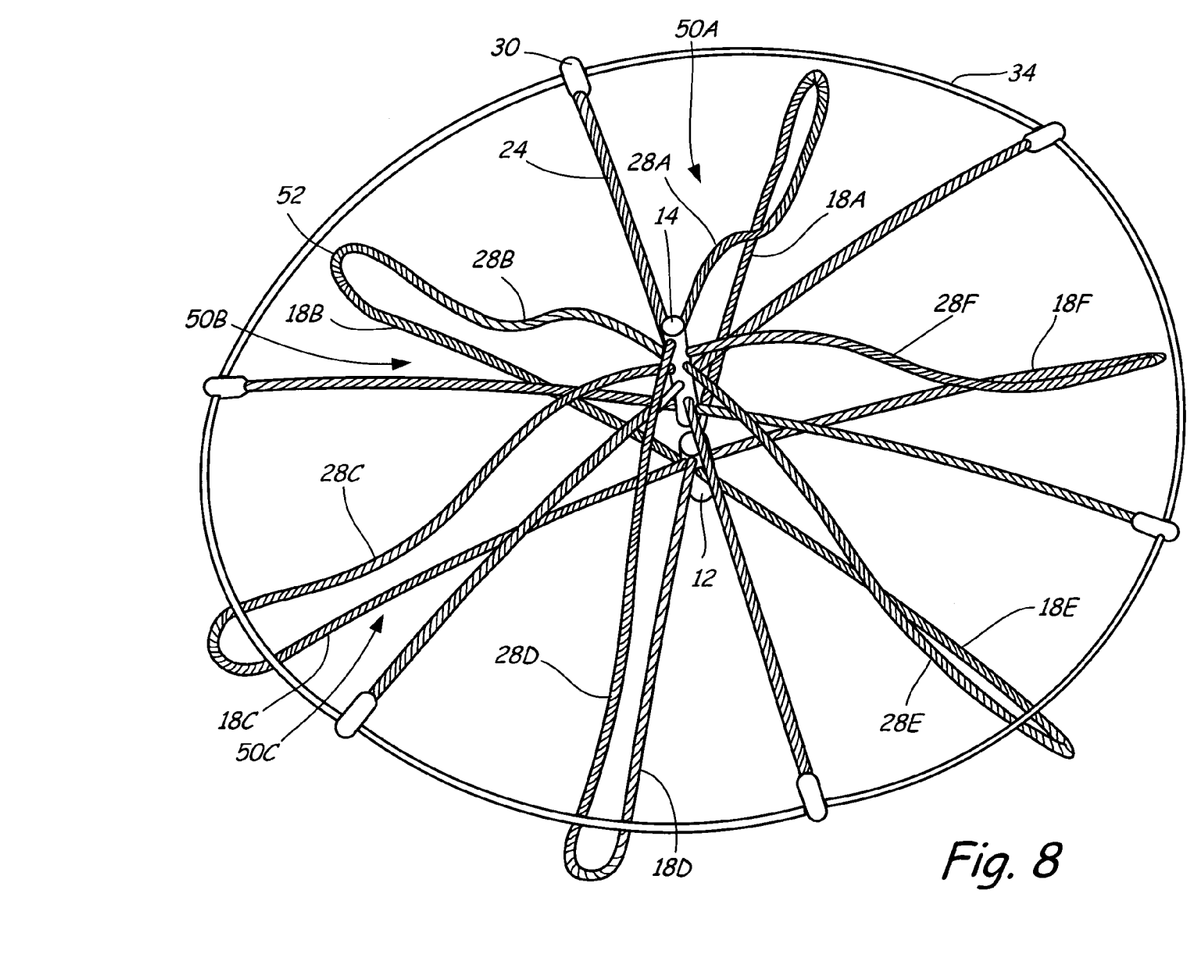
FIG. 8 is a perspective view of a frame of an occlusion device having a hoop on its left side and centering arms and right arms formed of three wires.

FIG. 8 is a perspective view of a frame for an occlusion device having hoop 34 on its left side. In the exemplary embodiment shown in FIG. 8, right arms 18A-18F and centering arms 28A-28F are formed of three wires 50A-50C. As discussed with reference to FIG. 6, left arms 24 terminate in end caps 30, which are connected to hoop 34. Wires 50A-50C include bend areas 52.

Each wire 50A-50C extends radially outward from left center post 14, bends at bend area 52 to extend through right center post 12, extends radially outward from right center post 12, and bends at bend area 52 to extend back into left center post 14. Wires 50A-50C may be attached to left center post 13 using any suitable method. As shown in FIG. 8, wires 50A-50C are attached to left center post 14 by inserting the ends of wires 50A-50C in one of six drill holes provided on left center post 14. Left center post 14 is then crimped to retain wires 50A-50C. Wires 50A-50C also pass through drill passages formed in right center post 12.

Each wire 50A-50C forms two right arms 18A-18F and two centering arms 28A-28D. For instance, wire 50A extends radially from distal center post to form right arm 18A. It then bends downward at bend area 52 and extends radially inward towards right center post 12 to form centering arm 28A. After passing though right center post 12, wire 50A extends radially outward to form centering arm 28D. Wire 50A then bends upward at bend area 52 and extends radially inward toward left center post 14 to form right arm 18D. Likewise, wire 50B forms right arm 18B, centering arms 28B and 28E, and right arm 18E. Wire 50C forms right arm 18C, centering arms 28C and 28F, and right arm 18F.

Wires 50A-50C may be made of any suitable biocompatible material. However, wires 50A-50C are preferably made of a material capable of shape memory, such as Nitinol. One suitable method of forming bend areas 52 when wires 50A-50C are formed of Nitinol, is to modify the physical properties of wires 50A-50C with an annealing cycle. When using this method, the portions of wires 50A-50C which will become bend areas 52 are exposed to heat ranging from about 500 degrees Celsius to about 700 degrees Celsius. The heat causes wires 50A-50C to bend in the desired area, thus forming bend areas 52. Forming right arms 18A-18F and centering arms 28A-28F from wires 50A-50C eliminates the need for a connection means between right arms 18A-18F and centering arms 28A-28F.

Although the present invention has been described with reference to preferred embodiments, workers skilled in the art will recognize that changes may be made in form and detail without departing from the spirit and scope of the invention.

The invention claimed is:
1. An occlusion device having a proximal end and a distal end, the occlusion device comprising:
 a right center post located at the proximal end of the occlusion device, the right center post having distal and proximal ends;

a left center post located distally from the right center post, the left center post having distal and proximal ends;

a plurality of right arms attached to the right center post which collapse when the right center post is pulled proximally;

a plurality of left arms attached to the proximal end of the left center post; and a plurality of centering arms emanating from the distal end of the left center post, each centering arm having an outer end portion which connects to an outer end portion of a right arm and wherein the plurality of centering arms define a flexible intermediate zone to center the occlusion device in an aperture.

2. The occlusion device of claim 1 and further comprising:
an end cap located at the outer end portion of each right arm.

3. The occlusion device of claim 2 and further comprising:
an end cap located at the outer end portion of each centering arm.

4. The occlusion device of claim 3 wherein the plurality of centering arms and the plurality of right arms are connected by a loop extending from the end cap of each centering arm to the end cap of a corresponding right arm.

5. The occlusion device of claim 4 wherein the loop comprises a metal wire.

6. The occlusion device of claim 3 wherein the plurality of centering arms and the plurality of right arms are connected by a pivotal joint formed between the end cap of each centering arm and the end cap of a corresponding right arm.

7. The occlusion device of claim 1 wherein the plurality of centering arms and the plurality of right arms are formed of three wires such that each wire defines two centering arms and two right arms.

8. The occlusion device of claim 7 and further comprising:
a plurality of bend areas located between the outer end portion of each centering arm and the outer end portion of a corresponding right arm.

9. The occlusion device of claim 8 wherein the plurality of bend areas are formed by exposing an area of each wire to heat.

10. The occlusion device of claim 1 and further comprising:
a continuous wire hoop positioned at outer end portions of the left arms.

11. The occlusion device of claim 10 and further comprising:
an end cap located at the outer end portion of each left arm for attaching the hoop to the left arms.

12. The occlusion device of claim 1 wherein the plurality of left arms, the plurality of centering arms, and the plurality of right arms are formed of stranded wire.

13. The occlusion device of claim 12 wherein the plurality of right arms are attached to the right center post by inserting each right arm into a drill hole provided on right center post.

14. The occlusion device of claim 1 wherein each of the plurality of right arms is formed of a single wire.

15. The occlusion device of claim 14 wherein the plurality of right arms is attached to the right center post by inserting an inner end portion of each right arm into a cavity formed in the distal end of the right center post and crimping the right center post to retain the inner end portions.

16. The occlusion device of claim 1 and further comprising first and second polyvinyl alcohol foam sheets attached to the plurality of right arms and the plurality of left arms, respectively.

17. The occlusion device of claim 1 wherein the plurality of centering arms form a bell-like shape when the right center post is pulled.

18. An occlusion device having a proximal end and a distal end, the occlusion device comprising:
right and left floating center posts, the right center post being located at the proximal end of the occlusion device and the left center post being located distally from the right center post;

a plurality of right arms attached to the right floating center post which collapse when the right center post is pulled in a proximal direction;

a plurality of left arms attached to a proximal end of the left floating center post;

a plurality of centering arms emanating from a distal end of the left floating center post, each centering arm having an outer end which connects to an outer end of a right arm wherein the plurality of centering arms extend through and center the occlusion device in an aperture; and a first sheet attached to the plurality of right arms which collapses when the right floating center post is pulled in a proximal direction.

19. The occlusion device of claim 18 and further comprising a second sheet attached to the plurality of left arms.

20. The occlusion device of claim 19 wherein a length of the plurality of centering arms correspond to a size of the aperture.

* * * * *